(12) United States Patent  (10) Patent No.: US 6,659,675 B2
Rew  (45) Date of Patent: *Dec. 9, 2003

(54) DOCUMENT FOLDER

(76) Inventor: David R Rew, 17B Wiggins Farm Dr., Simsbury, CT (US) 06070

( * ) Notice: Subject to any disclaimer, the term of this patent is extended or adjusted under 35 U.S.C. 154(b) by 0 days.

This patent is subject to a terminal disclaimer.

(21) Appl. No.: 10/266,014

(22) Filed: Oct. 7, 2002

(65) Prior Publication Data

US 2003/0039505 A1 Feb. 27, 2003

Related U.S. Application Data

(63) Continuation of application No. 09/741,606, filed on Dec. 19, 2000, now Pat. No. 6,461,070, which is a continuation-in-part of application No. 09/200,438, filed on Nov. 27, 1998, now abandoned, application No. 10/266,014, which is a continuation-in-part of application No. 09/292,030, filed on Apr. 16, 1999, now abandoned.
(60) Provisional application No. 60/067,957, filed on Dec. 8, 1997.

(51) Int. Cl.[7] ................................................. B42F 13/08
(52) U.S. Cl. ..................... 402/17; 40/359; 206/459.5; 229/67.1; 402/70
(58) Field of Search .................... 40/359; 206/425, 206/459.5; 229/67.1, 67.3, 75, 92.8; 283/37, 38, 39, 40, 41, 42, 43; 402/13, 14, 15, 16, 8, 9, 18, 60, 70, 75

(56) References Cited

U.S. PATENT DOCUMENTS

| | | | |
|---|---|---|---|
| 754,048 A | 3/1904 | Bushnell, Jr. | |
| 3,026,876 A | 3/1962 | Peynado | |
| 3,466,133 A | 9/1969 | Lennartz | |
| 5,087,162 A | 2/1992 | Basler | |
| 5,104,250 A | 4/1992 | Pacione | |
| 5,174,556 A | 12/1992 | Taylor et al. | |
| 5,213,433 A | 5/1993 | An | |
| 5,236,121 A | 8/1993 | Wollman et al. | |
| 5,407,230 A | 4/1995 | Brink et al. | |
| 5,445,468 A | 8/1995 | Pacione | |
| 5,562,309 A | 10/1996 | Brink et al. | |
| 5,607,246 A | 3/1997 | Podosek | |
| 5,613,791 A | 3/1997 | Mendenica | |
| 5,711,627 A | 1/1998 | Chapman | |
| 5,720,565 A | 2/1998 | Benson | |
| 5,724,075 A | 3/1998 | Smith | |
| 5,897,141 A | 4/1999 | Dugmore et al. | |
| 5,961,150 A | 10/1999 | Kogutt et al. | |
| 6,017,164 A | 1/2000 | Abbott | |
| 6,236,767 B1 | 5/2001 | Altman | |
| 6,461,070 B2 * | 10/2002 | Rew | 402/60 |

* cited by examiner

Primary Examiner—Monica Carter

(57) ABSTRACT

A document folder has a cover formed of relatively flexible sheet material with a back and front panels, and a spine hingedly connecting the panels so that they may be disposed in an overlying position and provide an enclosure for documents therebetween. The panels are movable relative to each other about the spine, and disposed therebetween is a relatively rigid stiffener dimensioned cooperatively with the back panel to rigidify the folder when stored vertically. A document holder is engaged with the stiffener for securing a multiplicity of documents between the stiffener and the front panel. The cover may be integrally formed or assembled from separate panels, one of which provides the spine. At least a portion of the cover is formed from a material which may be imprinted in a computer printer.

13 Claims, 13 Drawing Sheets

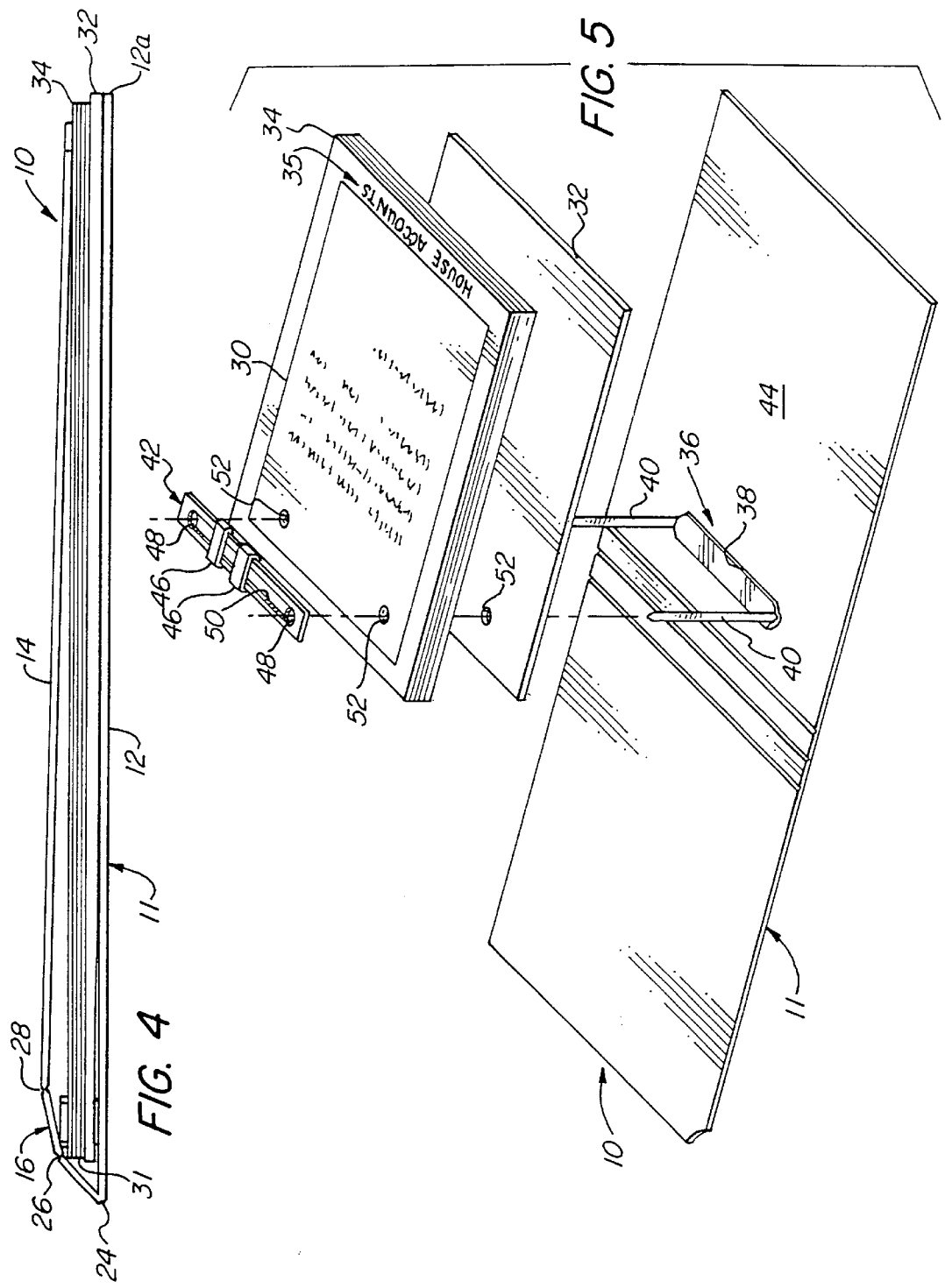

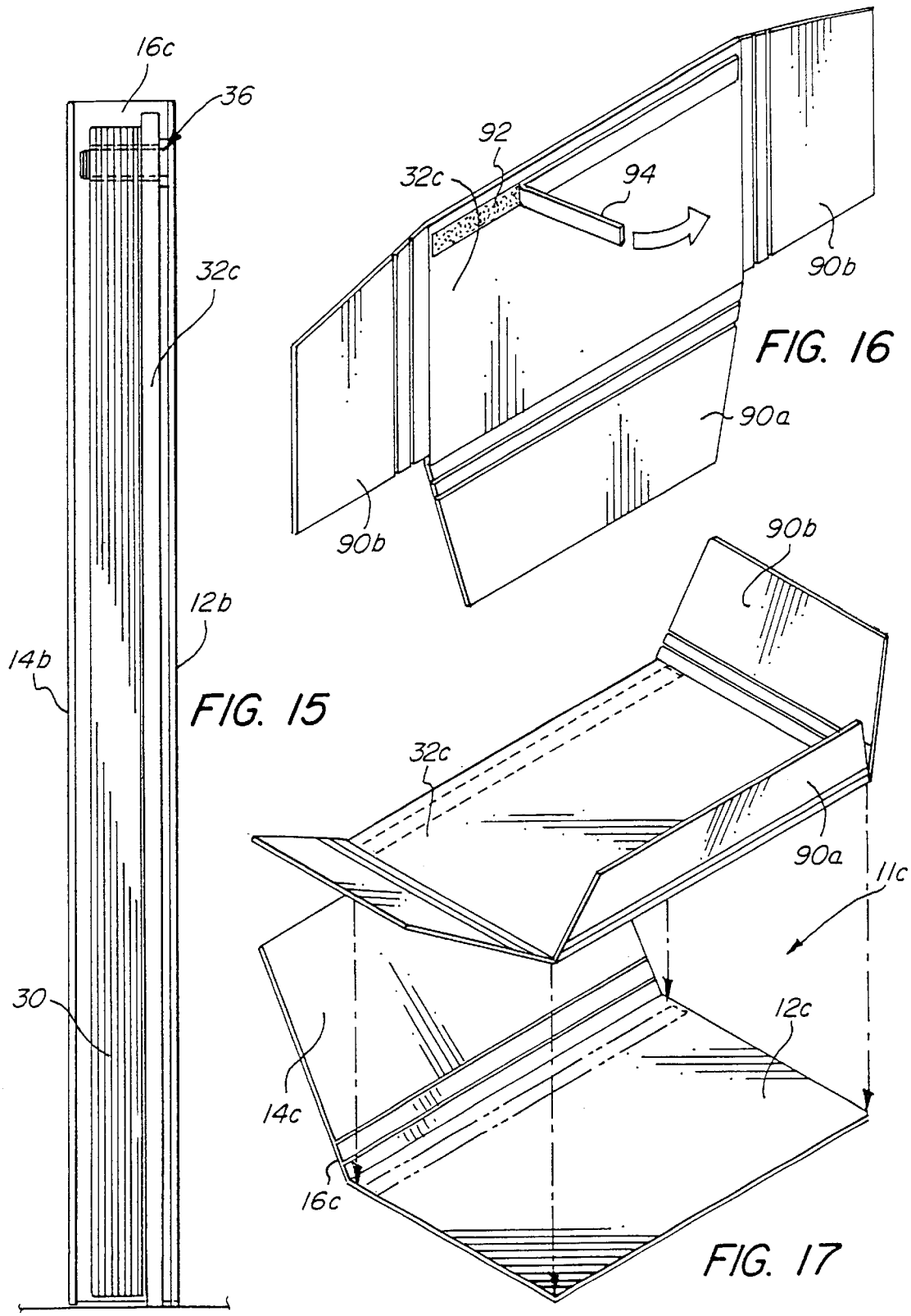

DOCUMENT FOLDER

CROSS REFERENCE TO RELATED APPLICATION

The present application is a continuation-in-part of my application Ser. No. 09/292,030 filed Apr. 16, 1999 which is now abandoned, a continuation of my application Ser. No. 09/741,606 filed Dec. 19, 2000 now U.S. Pat. No. 6,461,070 which will issue on Oct. 8, 2002, which is a continuation-in-part of application Ser. No. 09/200,438 filed Nov. 27, 1998 which is now abandoned, and which claims the benefit of Provisional Application Serial No. 60/067,957 filed Dec. 8, 1997.

BACKGROUND OF THE INVENTION

The present invention relates to document folders and, more particularly, to folders into which documents are easily inserted and removed from, and which may be stored in erect position in a row of folders when individual folders are vertically positioned in horizontally extending rows.

Document or file folders, e.g., manila folders, are well known and are employed for collecting, accumulating, and indexing or segregating a plurality of related documents in a unitary volume. Typical applications for document folders include bundling and indexing legal documents and retail sales records. In retail specialty sales, sales receipts are kept as a record of business transactions for each day for financial reasons and as a record of a customer's instructions concerning an order.

The receipts thereby provide a record of customers' orders which may be referred to for various purposes, including the filling of repeat orders. This type of repeat order transaction is common in the retail florist industry. For example, many customers order flowers or floral arrangements simply by asking for the same arrangement of flowers that was sent on a particular previous occasion. Thus, most retail florists keep extensive records comprising copies of daily retail sales slips, organized in chronological, or other, order. Such records may be kept in a document folder which provides a ready reference for sales persons when a customer requests a repeat of a previous order.

The document folders in which the sales receipts are bundled may be kept in a drawer or a filing cabinet.

Similarly, professionals such as physicians maintain file folders into which they insert documents relating to patients and wish to maintain them in chronological or other specific order for repeated reference. Lawyers store documents in folders which separate by client, matter and subject.

Generally, file folders are stored in horizontal or vertical file drawers and have tabs with indicia placed thereon to facilitate their identification. These tabs can be readily damaged because they are relatively small projections and the card stock is easily bent, and the size limits the amount of information which can be printed thereon.

In some applications, the most active file folders are stored in open top trays or boxes for easy access, but the same problems of identification and potential damage to the tab occurs.

Order form booklets are a form of document file which can present special problems in that it is sometimes desirable to place loose copies of documents therein, and these may fall out when the folder is removed from the storage area.

Moreover, many document folders employ paper board stock which is so flexible that the folder does not have sufficient stiffness to stand vertically without lateral support.

With the widespread use of computers and associated printers, label or file titles are frequently stored in computer memory and used to print identifying information on various documents. Generally, this requires printing of labels which are then adhered to the file folders and which are frequently damaged or fall off.

It is an object of the present invention to provide a method for imprinting a novel document folder in which multiple document can be readily assembled and stored and which is relatively rigid so that it is self-supporting in an upright position when stored against a vertical surface.

It is also an object to provide a novel document folder kit for use in such a method.

Another object is to provide such a document folder kit in which there is a portion of large area in a position which is visible in its stored position and upon which identifying indicia may be printed utilizing conventional computer printers.

SUMMARY OF THE INVENTION

It has now been found that the foregoing and related objects may be readily attained in a document folder for enclosing and retaining a multiplicity of documents comprising a cover formed of relatively flexible sheet material and having a back panel, a front panel and a spine hingedly connecting the panels. The panels are disposable in an overlying position and, together with the spine, provide an enclosure for receiving a multiplicity of documents therebetween, and the panels are movable relative to each other about the spine. Also included are a relatively rigid stiffener dimensioned cooperatively with the back panel to rigidify the folder when stored vertically so that it is self-supporting and document securing means engaged with the stiffener for securing a multiplicity of documents between the stiffener and the front panel.

Generally, the stiffener is substantially coextensive with the back panel, and conveniently it is adhesively engaged with the back panel. In some embodiments, the securing means comprises a fastener having a center portion with a pair of prongs at its ends which are adapted to extend through apertures in the stored documents. The center portion is conveniently mounted on the back panel and the prongs extend through apertures in the stiffener to secure it thereto.

In one embodiment, the back panel has an overlying flap along one side thereof and the fastener is secured to the overlying flap. The front panel is separately formed and has a flap along one side thereof which overlies the flap of the back panel, and the front panel flap has apertures therein through which the prongs extend.

In another embodiment, the center of the fastener portion is mounted on the stiffener which is adhered to the back panel.

In some embodiments, the cover is integrally formed. In others, the front and back panels are separate elements with the spine being integrally formed with one of the panels.

Other securing means include a clamp mounted on the stiffener, a ring binder element mounted on the stiffener, and a pocket forming element on the stiffener.

The spine may have a plurality of fold lines extending longitudinally thereof whereby the spine may be varied in width to vary the spacing between the panels.

Desirably, at least the spine is adapted to be imprinted with indicia viewable when stored in a file.

In some embodiments, the back panel has side flaps hingedly connected thereto along the side margins thereof and an end flap hingedly connected to its end opposite the spine, the side and end flaps being foldable into a position overlying the back panel to provide a pocket. The front panel may be releasably engageable with the end flap, and the side and end flaps may have a plurality of fold lines extending longitudinally thereof adjacent the back panel whereby the spacing between the overlying portions of the flaps and the back panel may be varied.

The folder may include a plurality of dividers for separating the documents on the stiffener into groupings. The center portion of the fastener may be adhesively engaged with the inner surface of the back panel and have its prongs extending through the stiffener.

Preferably, the folder is dimensioned so that it may be fed through a computer printer. The material from which the folder is formed should be printable in a computer printer. When the folder is formed of separate panels, at least the spine should be printable.

BRIEF DESCRIPTION OF THE DRAWINGS

FIG. 4 is a side elevational view of the folder of FIG. 1 drawn to an enlarged scale;

FIG. 5 is an exploded view of the folder of FIG. 1 with the front flap opened and the clamp element removed;

FIG. 15 is an elevational view of the folder of FIG. 14 with documents assembled therein;

FIG. 16 is another embodiment of the present invention in which the stiffener has a series of flaps formed thereon which are foldable into overlying position to provide a pocket in which documents are stored;

FIG. 17 is a partially exploded view of the insert of FIG. 16 prior to engagement on the rear panel of the folder;

DETAILED DESCRIPTION OF THE PREFERRED EMBODIMENTS

Figure 1:
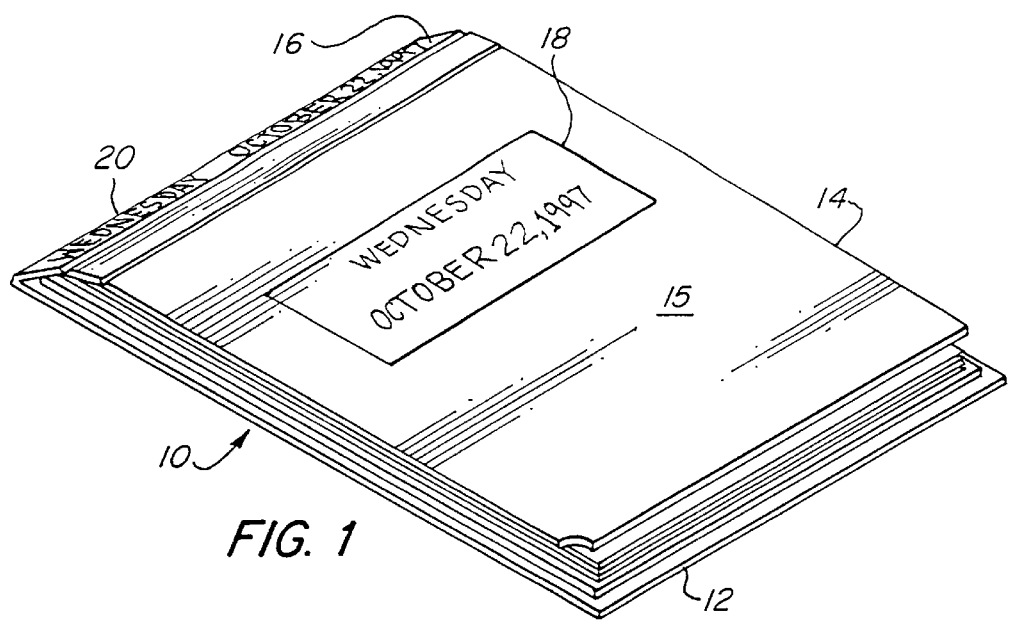
FIG. 1 is a perspective view of a document folder embodying the present invention.

A document folder in accordance with the present invention is generally designated by the numeral 10 in FIG. 1. The document folder 10 includes a cover generally designated by the numeral 11 with a back panel 12 and a front panel 14. The back panel 12 and front panel 14 are movable relative to each other and connected to each other by means of the spine 16 at their upper ends. The cover 11 is fabricated from relatively flexible sheet material such as heavy gauge paper or paperboard, or plastic, e.g., a polyolefin or other resin which may be imprinted. Suitable indicia 18 may be provided on the front panel 14 for identifying the subject matter and/or date range of the documents contained within the folder. The spine 16 (and the panels) may also be imprinted with indicia 20 so that they are visible when the folder 10 is placed in a file.

Figure 2:
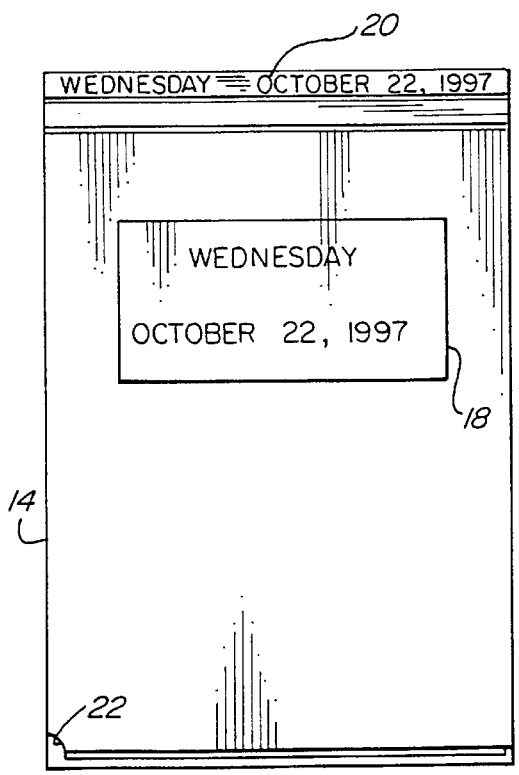
FIG. 2 is a plan view of the front face of the folder of FIG. 1.

As illustrated in FIG. 2, the front panel 14 may include a notched portion 22. The notched portion 22 may be useful to thumb to a particular document or documents contained within the document folder 10 by, for example, indexing tabs or the like (not shown).

Figure 3:
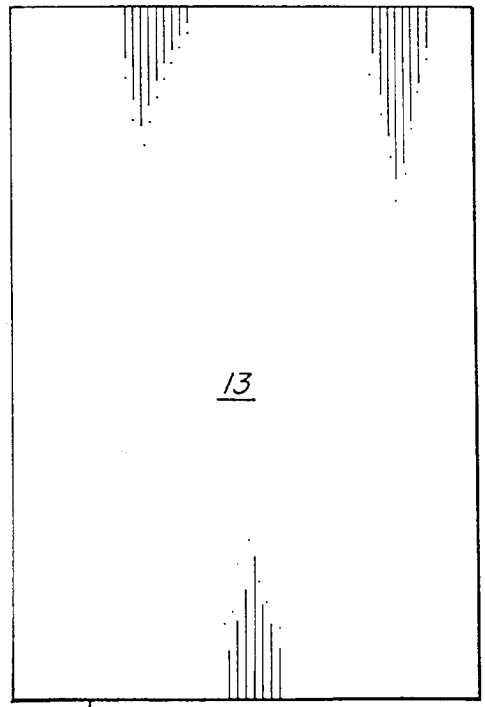
FIG. 3 is a plan view of the rear face of the folder of FIG. 1.
Figure 6:
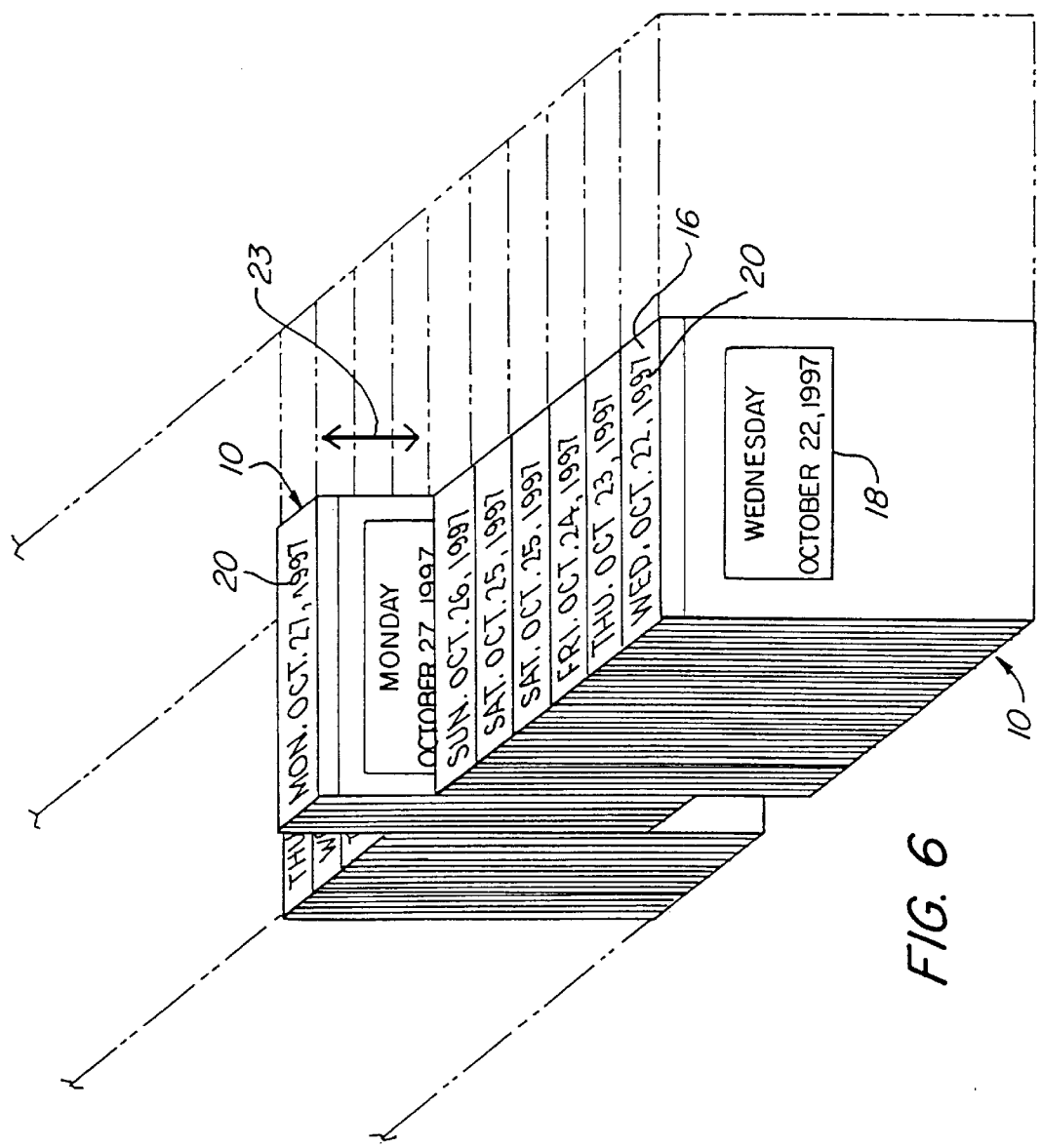
FIG. 6 is a schematic perspective view of a plurality of document folders of FIG. 1 arranged vertically in a plurality of rows.

As shown in FIGS. 1, 3 and 6, the back panel 12 and the front panel 14 include smooth outer surfaces 13, 15 for ease in stacking the document folders 10, e.g., in a container such as a filing cabinet (not shown). By stacking the document folders 10 in rows in the illustrated upright position, indicia 20 are viewable, and space in the file drawer or container is conserved. Referring to FIG. 6, the document folders may be stacked, e.g., in a plurality of rows in a storage container of suitable width whereby, because of the smooth outer surfaces of the back and front flaps 12 and 14, individual document folders 10 may be readily inserted into, and removed from, a row as indicated by the arrow 23.

The front cover and spine are imprintable using general purpose office equipment. This requirement limits the size, shape, thickness and other characteristics of the sheet material use. The shape of the material must be rectangular with straight contours to feed to squarely into the printer. The most popular office printers in the United States are limited in size to letter/legal size (8½"×14") and tabloid (13"×19") and in thickness to about 0.3 mm. The material cannot be rigid, and the surface of the material must not repel the ink or toner. Most office printers leave at least a ¼" margin that cannot be imprinted, and this means that a ⅜" spine should be well inside the edge of the sheet to ensure proper printing. Provided these constraints are met, any suitable material such as paper, plastic or parchment (leather) may be used for the entire cover, or the front panel and spine.

As best illustrated in FIG. 5, the spine 16 includes three fold lines 24, 26 and 28 formed by scoring or other well known techniques. They provide for varying of the distance between the panels 12, 14 to accommodate varying volumes of documents 30 (FIG. 5) within the document folder 10. The first fold line 24 is disposed advantageously a short distance away from an upper edge 31 of the documents 30 so as to allow for ease in folding of the front flap 14 thereover. As the number of documents pinned in the folder increases, the additional fold lines 26, 28 provide extra spacing. It will be appreciated that while three fold lines are shown for illustrational purposes, any suitable number may be employed.

Figure 29:
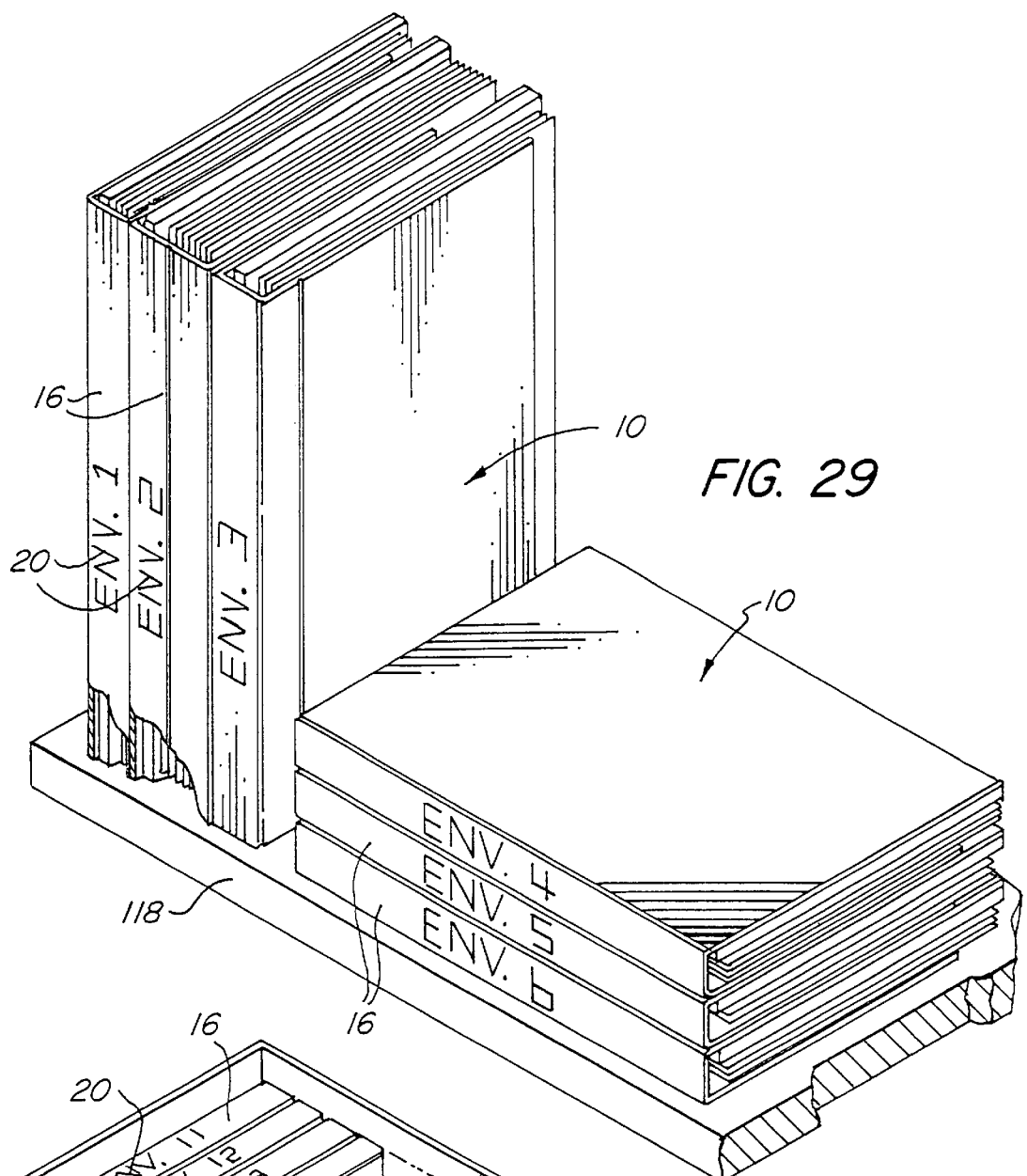
FIG. 29 is a perspective view showing a number of folders embodying the present invention and printed along the spine, some of the folders being stacked in an upright position and others lying in a horizontal position.
Figure 30:
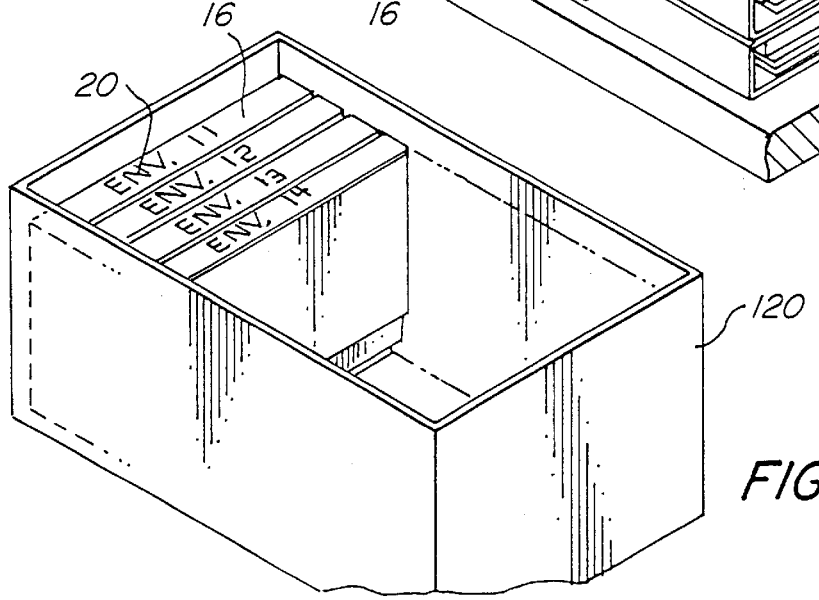
FIG. 30 is a fragmentary perspective view of a file drawer or carton in which a number of folders embodying the present invention are stored in upright position and have identifying indicia printed upon their spine.

As shown in FIGS. 4 and 5, the document folder 10 includes a stiffener 32 along with a plurality of document dividers 34. The stiffener 32 may be formed of any suitable sheet material that is relatively rigid or inflexible such as a plastic, e.g., a polyolefin, or a heavier gauge paperboard or cardboard. The stiffener 32 is employed to support the document folder 10 to make it self-supporting when placed in an upright or vertical position against a vertical surface or between vertical surfaces such as like folders 10 as seen in FIGS. 29 and 30 and as illustrated in FIG. 6. It will be appreciated that the dimensions of the stiffening member 32 and the back panel 12 are approximately coextensive to prevent folding or creasing damage to the bottom edge 12a of back flap 12 when the document folder 10 is in the upright position shown in FIG. 6. Also, by employing the stiffener 32, the cover 11 may be integrally formed, or formed of separate panels, of relatively thin material.

The dividers 34 are advantageously provided for separating various groups of documents 30 based upon, for example, a category of various methods of payment such as house accounts, credit cards or cash as illustrated by indicia 35. Physicians may separate tests from reports, etc.

A conventional two prong fastener generally designated by the numeral 36, usually made of a metal or plastic, is employed for retaining the documents together on the back flap. It includes a base 38, a pair of deformable prongs 40 and a clasp 42. The base 38 is preferably mounted on the inner surface 44 of the back panel 12 by any suitable means such as an adhesive or tape which does not protrude through the back flap 12. If elements of the fastener were to protrude through the back flap 12, such elements would interfere with smoothly withdrawing and inserting individual document folders 10 from and into a tightly packed row, as illustrated in FIG. 6. For this reason, front panel 14 as well as the back panel 12 are maintained smooth and free of protrusions of any kind. The clasp 42 includes apertures 48 and a groove 50 for receiving the prongs 40. A pair of sliders 46 are disposed on the clasp 42 and are selectively movable to lock the prongs 40 in place. The stiffener 32, dividers 34 and documents 30 include apertures 52 through which the prongs 40 extend for retention on the back panel 12 of the document folder 10.

Figure 7:
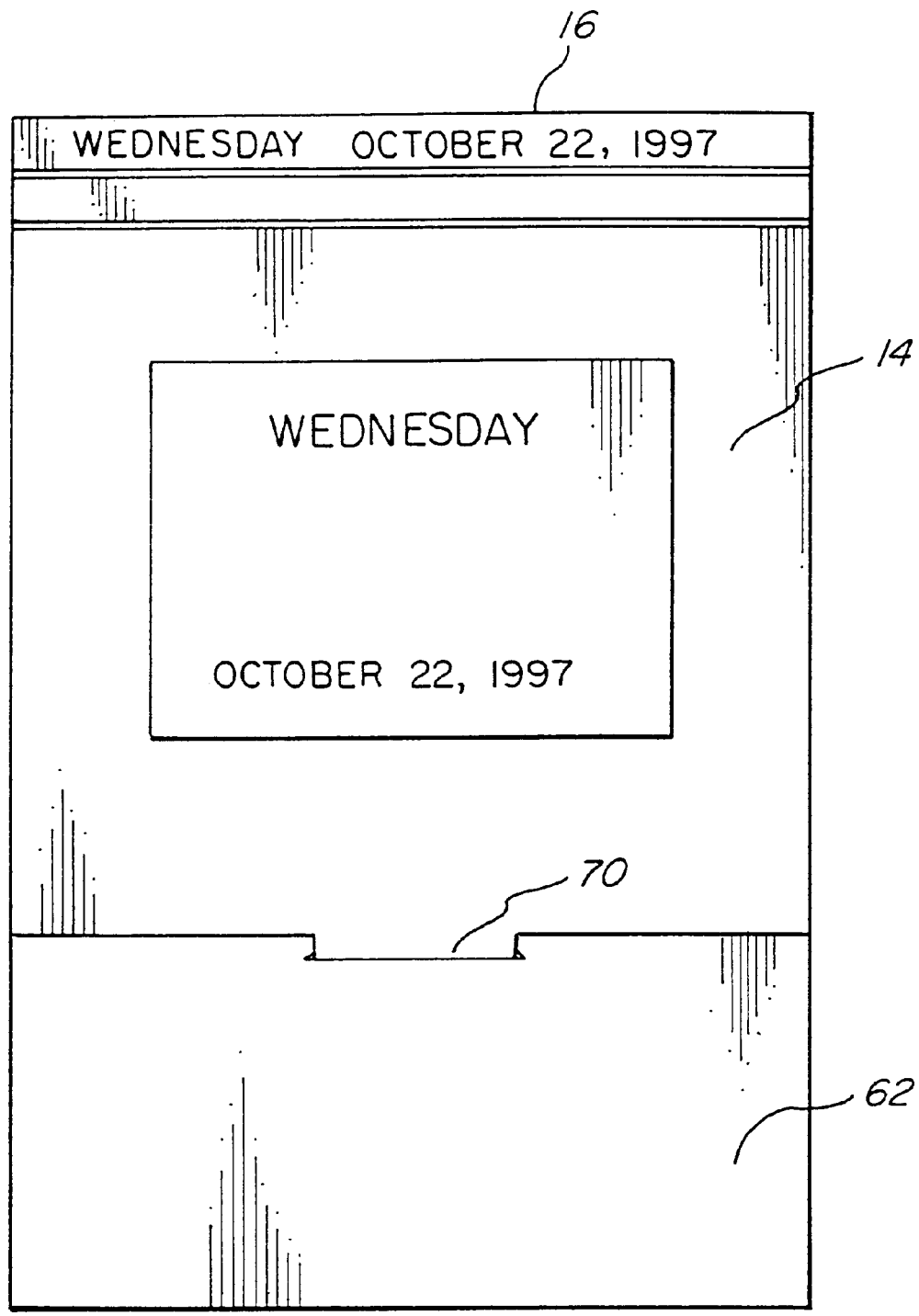
FIG. 7 is a plan view of the front face of another embodiment of the present invention.
Figure 8:
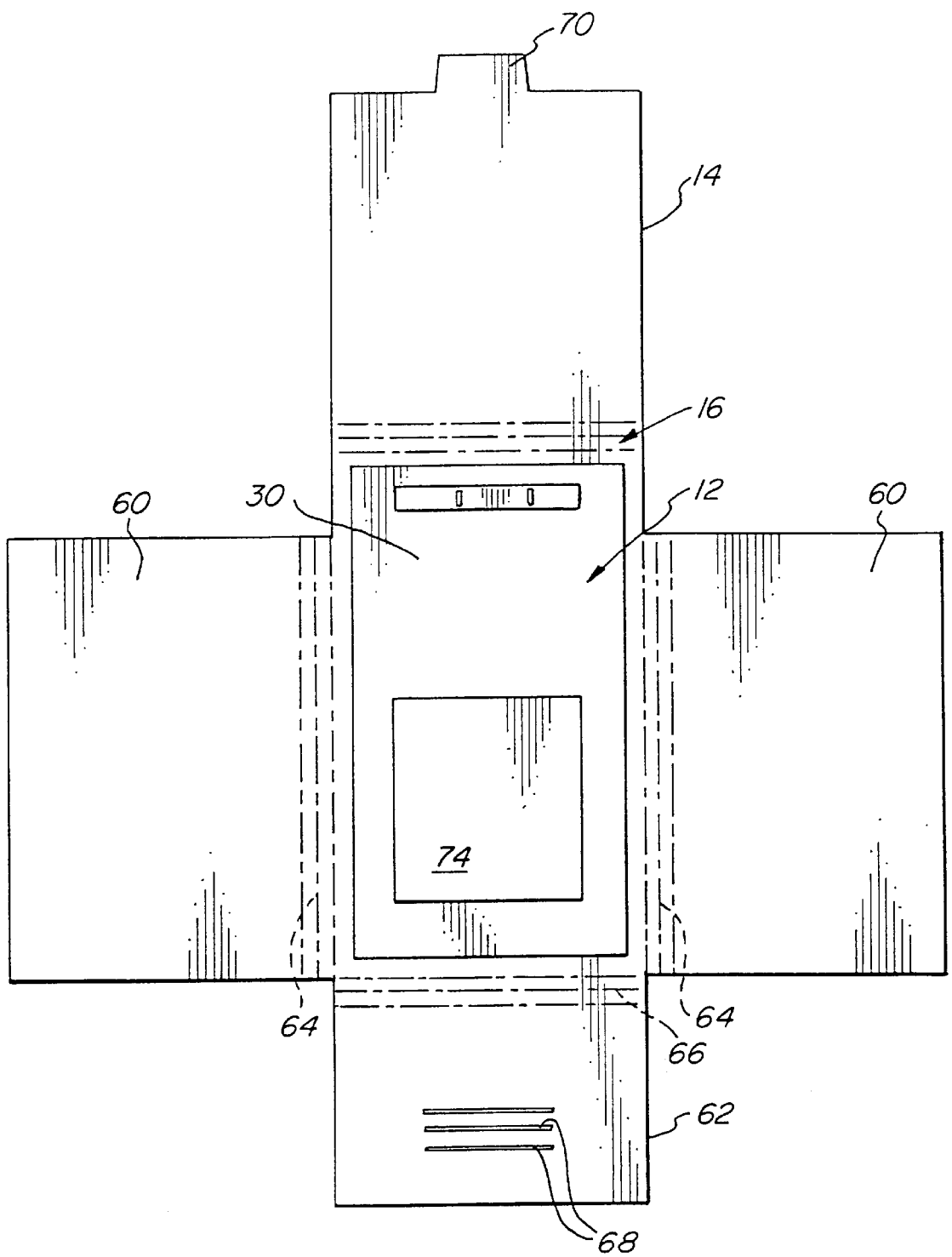
FIG. 8 is a plan view of the opened folder of FIG. 7.

Turning next to FIGS. 7 and 8 therein illustrated is another embodiment of the present invention which includes side and end flaps 60, 62 to provide a four-sided enclosure for any loose documents which might also be stored in the folder 10. In this embodiment, the back panel 12 has the side flaps 60 extending over most of the length thereof and provided with a series of fold lines 64 to enable adjustment of the width therebetween when folded over. Along the end of the back panel 12 opposite the spine portion 16 is the end flap 62 with a series of fold lines 66 and a series of parallel slits 68 therein.

In this embodiment, the front panel 14 is not coextensive with the back panel 12 and has a tab 70 formed at its free end which will, when the front panel 14 is folded over be engageable in one of the slits 68. In addition to the documents 30, loose papers 74 may be placed within the folder and will be retained therein by the side and end flaps 60, 62.

In subsequent illustrations, modifications of a previously numbered structural element may bear the same numeral but coupled with a letter modifier, e.g., 11a.

Figure 9:
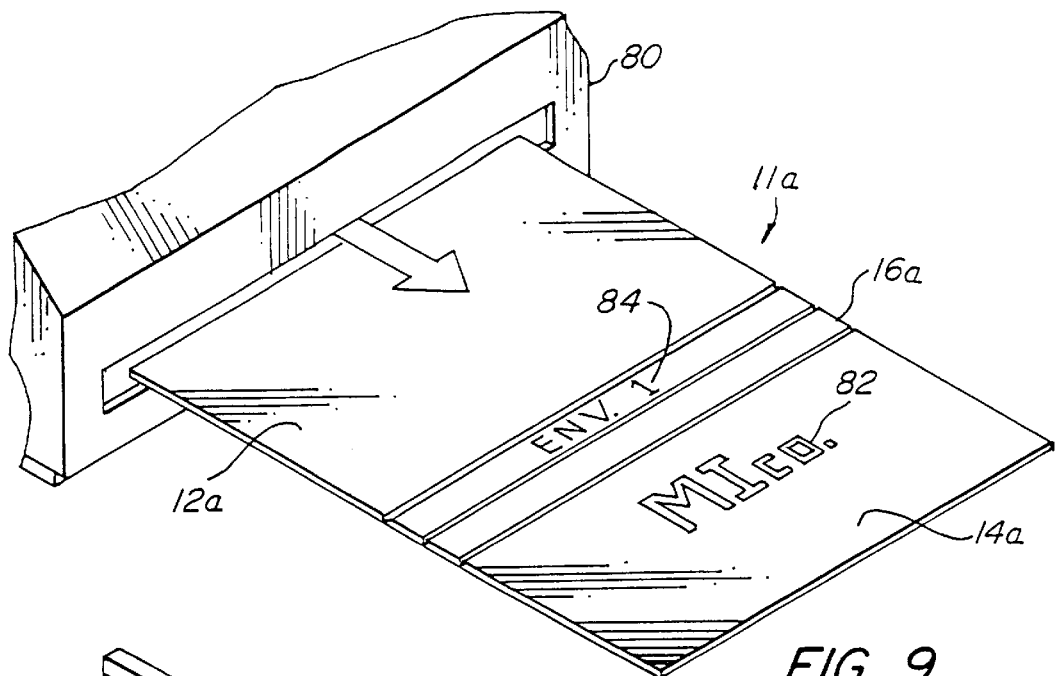
FIG. 9 is a partially diagrammatic view of a cover emerging from a fragmentarily illustrated computer printer wherein it has been imprinted with indicia.

In FIG. 9, a cover 11a is seen exiting from the fragmentarily illustrated computer printer 80 wherein it has been printed with indicia 82, 84.

Figure 10:
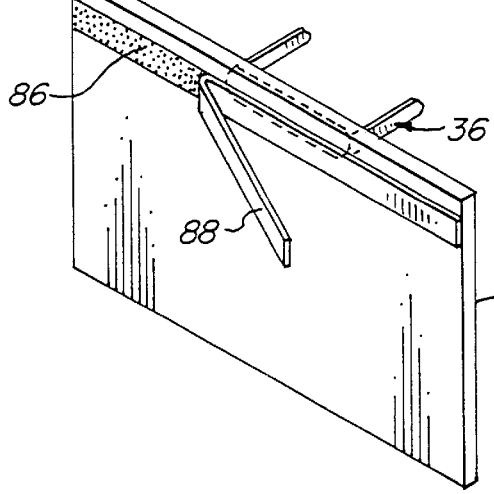
FIG. 10 is a perspective view of a stiffener with a release paper strip partially removed to expose a stripe of adhesive.
Figure 11:
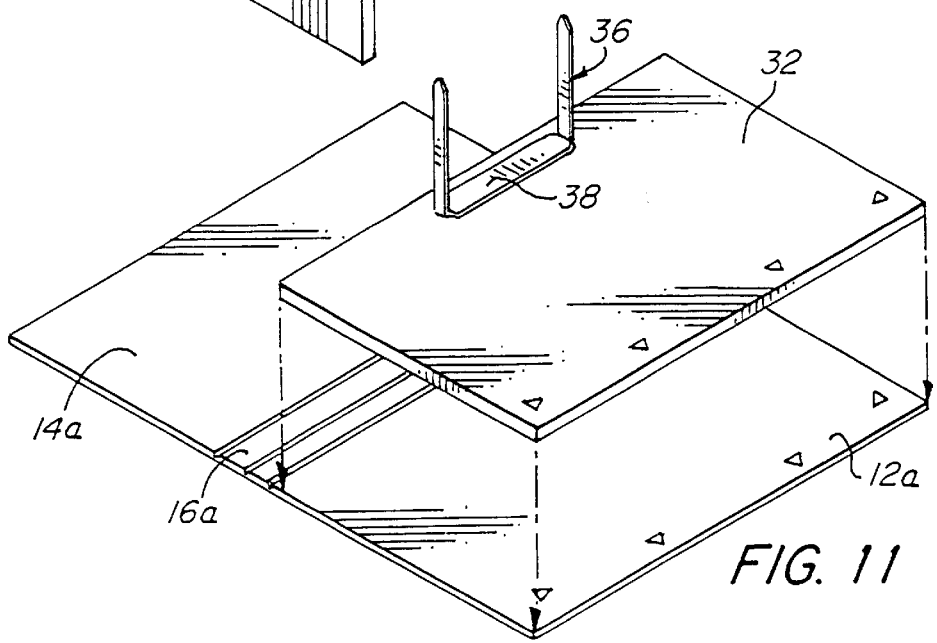
FIG. 11 is a perspective view of the cover of FIG. 9 with the stiffener of FIG. 10 aligned with the back panel of the cover prior to engagement thereon.
Figure 12:
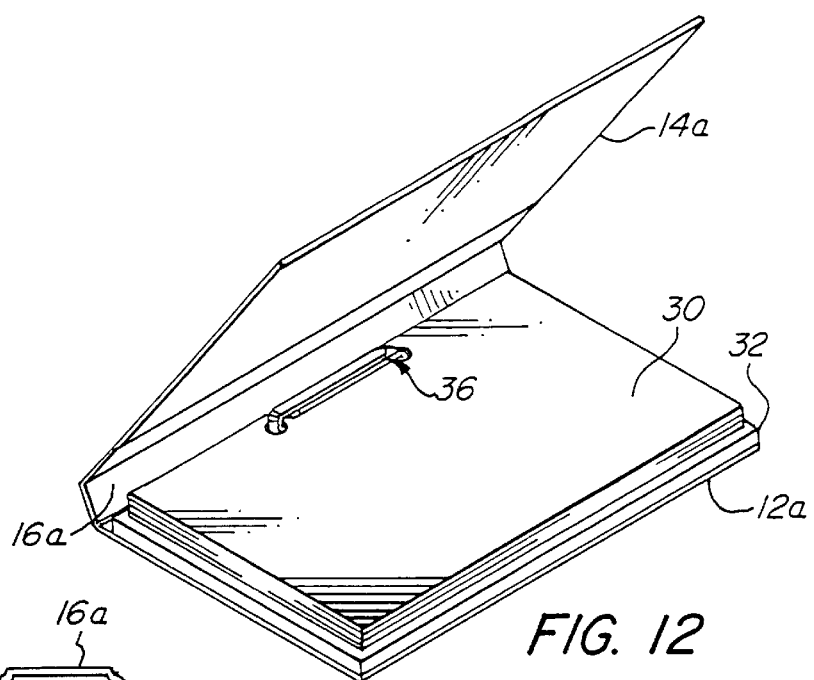
FIG. 12 is a perspective view of the partially opened folder embodiment of FIGS. 9–11 with a number of documents retained on the fastener within the folder.
Figures 13, 14:
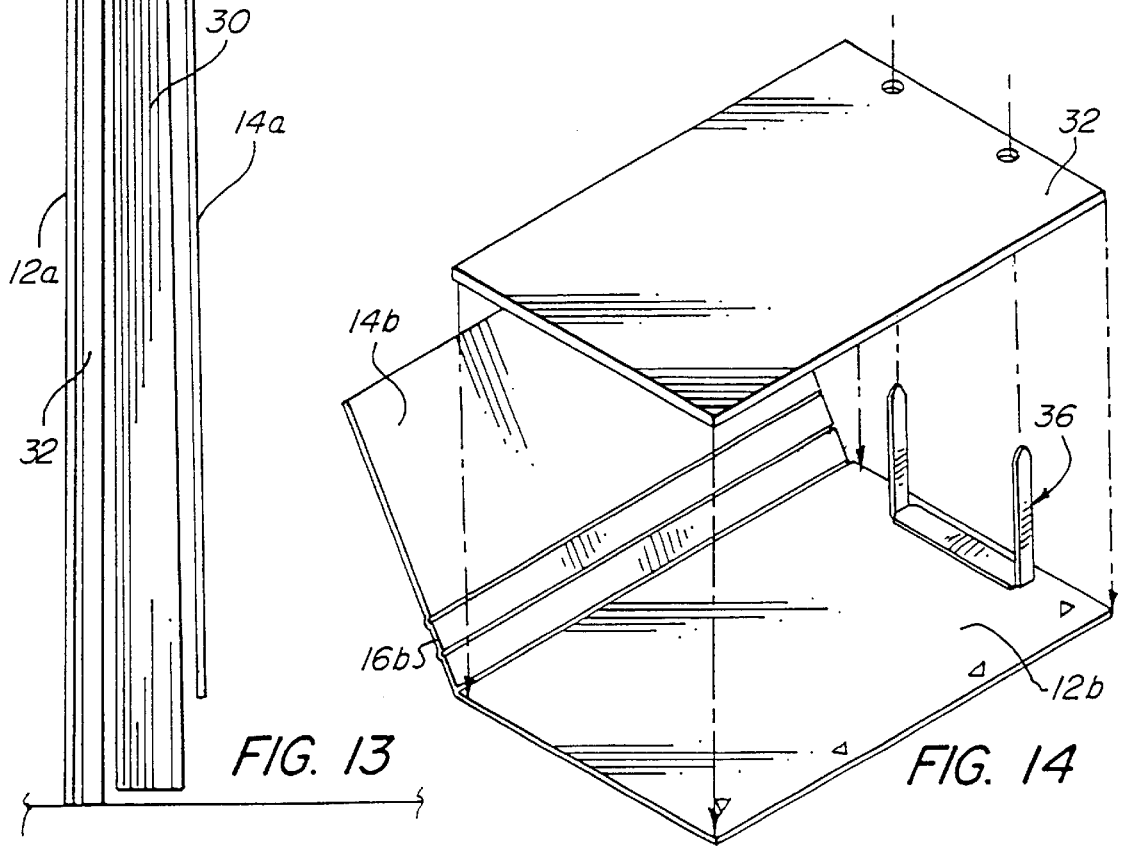
FIG. 13 is an end elevational view of the folder of FIG. 12 as stacked in an upright position.
FIG. 14 is a partially exploded perspective view of another embodiment of folder in which the fastener is secured to the back panel of the folder and extends upwardly through apertures in the stiffener.

In FIGS. 10 and 11, there is illustrated an alternate embodiment for the folder 10 of the present invention in which the rigidifying stiffener 32 is secured to the back panel 12a by a stripe of adhesive 86 which is covered by a release paper strip 88, and the two-prong fastener 36 has its base portion 38 adhered to the surface of the stiffener 32. In FIGS. 12 and 13, there is illustrated the embodiment of FIGS. 10 and 11 in which a number of documents 30 have been mounted upon the fastener 36.

Turning next to FIG. 14, it is basically similar to the first embodiment of the present invention. The fastener 36 is adhered to the back panel 12b along its short side and the spine 16b extends along the long side of the back panel 12b. In FIG. 15, the embodiment of FIG. 14 is shown with documents 30 therein and with the fastener 36 disposed in the upper most position and the spine 16b extending along vertically the side opposite that presented in the drawing.

Figure 18:
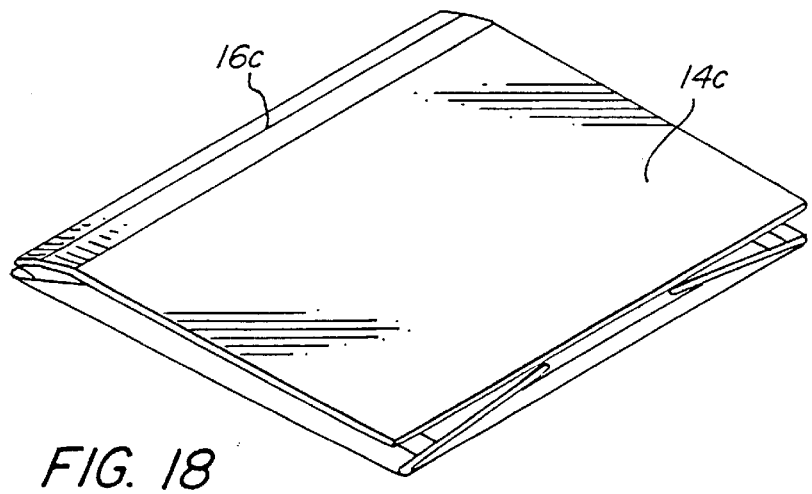
FIG. 18 is a perspective view of the closed folder of FIGS. 16 and 17.

Turning next to FIGS. 16 and 17, another embodiment of the folder of the present invention has the stiffener 32c formed with flaps 90 along three of its sides and it is provided with a stripe of adhesive 92 along its body portion. A release paper strip 94 covers the adhesive 92 until such time as it is desired to mount the stiffener 32c on the back panel 12c of the cover 11c. In this embodiment the documents 30 (not shown) are stored and held in position within the folder by the flaps 90. The closed document folder is illustrated in FIG. 18.

Figure 19:
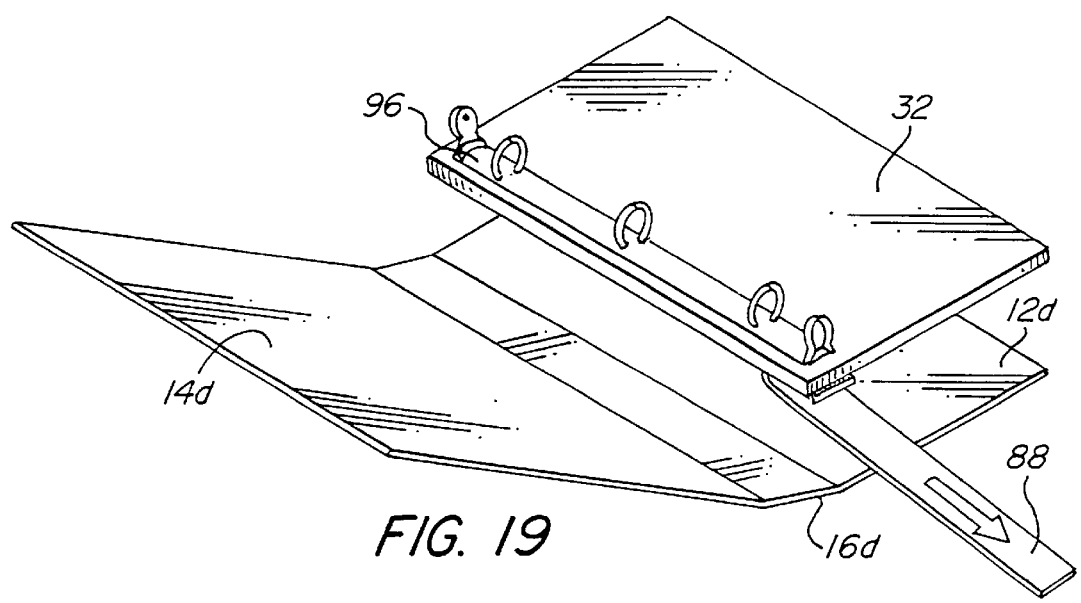
FIG. 19 is a partially exploded perspective view of another embodiment of the folder utilizing a ring binder mounted upon the stiffener which is to be secured to the back panel by an adhesive stripe.

In FIG. 19, there is illustrated an embodiment in which a 3-ring binder 96 is mounted upon the stiffener 32 which in turn is mounted upon the back panel 12d by an adhesive stripe (not shown) which is covered by the release paper strip 88.

Figure 20:
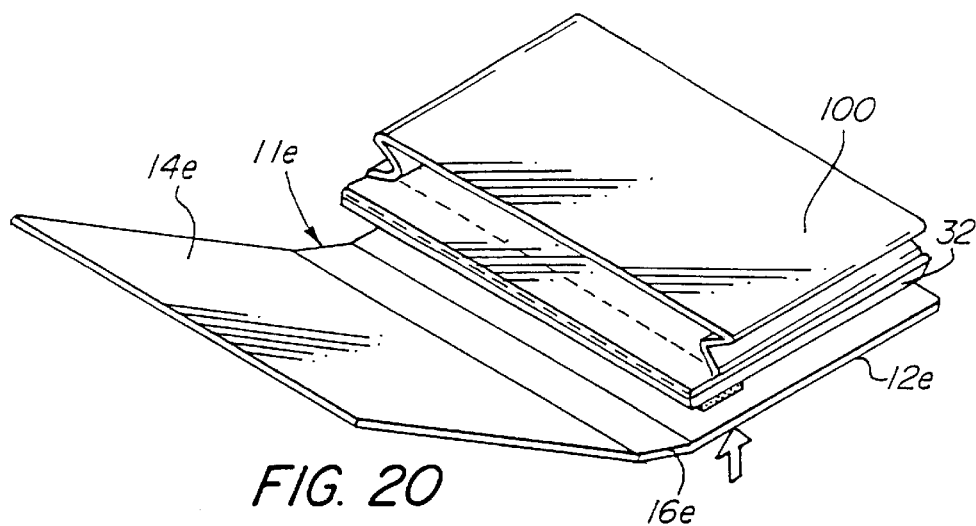
FIG. 20 is a partially exploded perspective view of still another embodiment of the folder of the present invention utilizing a stiffener which has adhered thereto an expandable pocket and which is to be secured to the back panel of the cover by an adhesive stripe.

FIG. 20 shows still another embodiment in which an expandable pocket 100 is adhesively bonded to the surface of the stiffener 32 which in turn is adhesively secured to the back panel 12e of the cover 11e.

Figure 21:
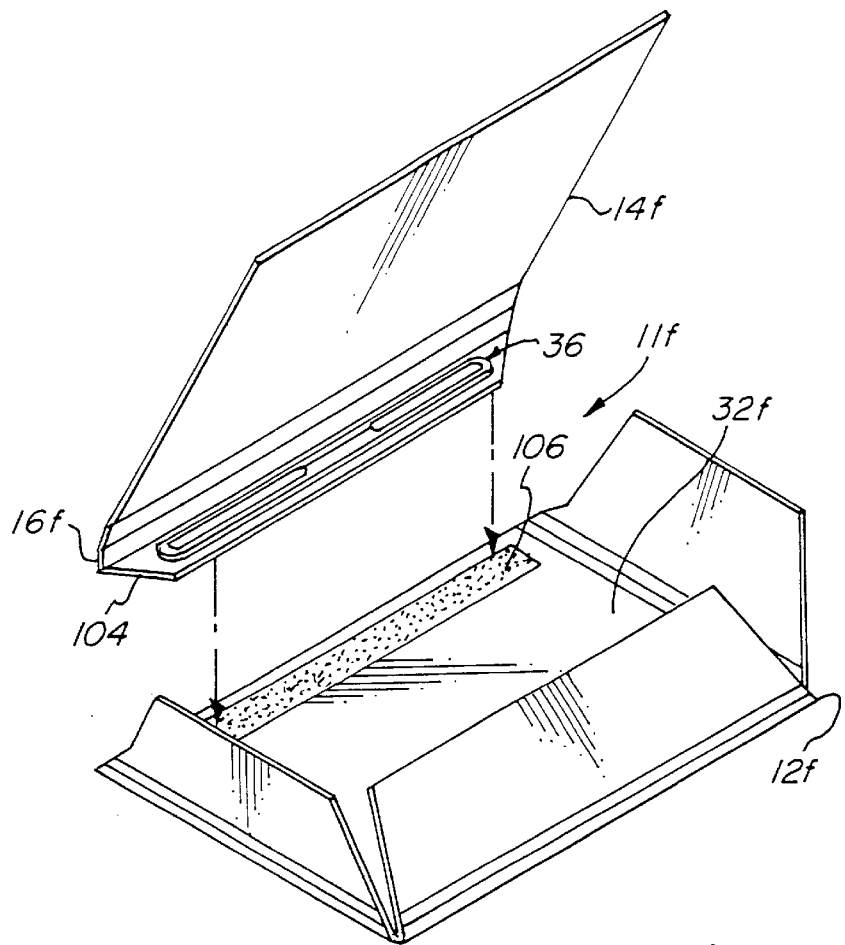
FIG. 21 is a partially exploded view of another embodiment having a cover assembled from separate front and back panels.

Turning next to FIG. 21, there in illustrated is a modification of the embodiment of FIGS. 16 and 17 wherein the cover 11f is fabricated from separate panel elements 12f, 14f with the front panel 14f providing the spine 16f and an inturned flap 104 by which it is secured to the stiffener 32f by a stripe of adhesive 106. As seen, the flap 104 has mounted thereon a fastener 36 to be utilized for the binding of the documents within the folder.

Figure 22:
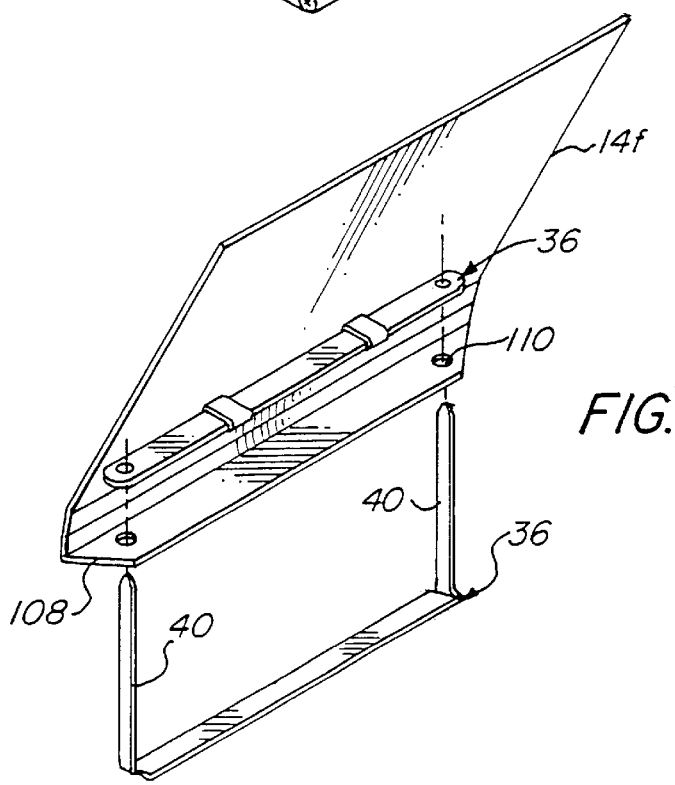
FIG. 22 is a partially exploded view of the front panel of this embodiment showing the separated base element of the fastener.

In FIG. 22, the base element of the fastener 36 can be seen separated from its clamp. The flap 108 on the front panel 14f has a pair of apertures 110 through which the prongs 40 extend. The flap 108 and the fastener 36 are secured to the stiffener 32 by adhesive 106.

Figure 23:
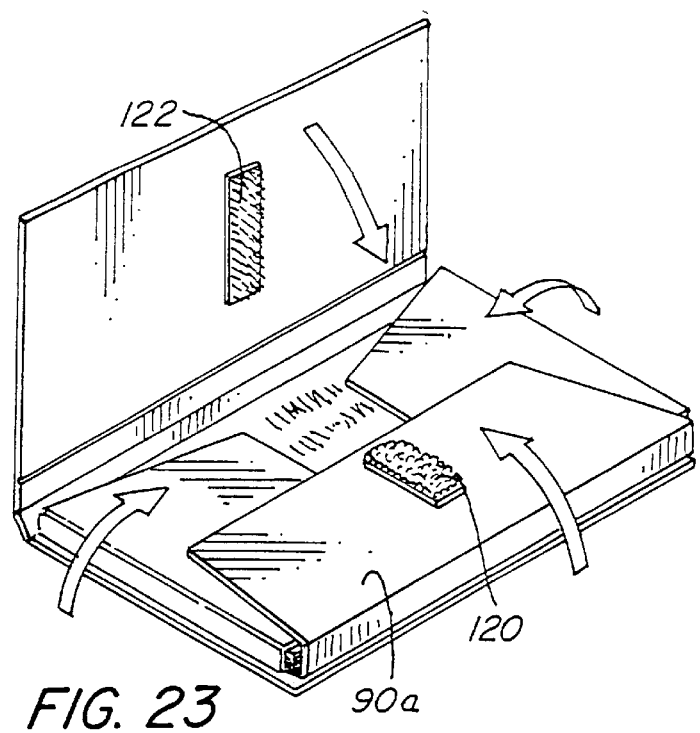
FIG. 23 is a perspective view showing a stiffener embodiment which has flaps formed thereon which can be folded into overlying position to define a pocket in connection with the body portion of the stiffener and employing engageable closure elements on a flap of the stiffener and front panel.
Figure 25:
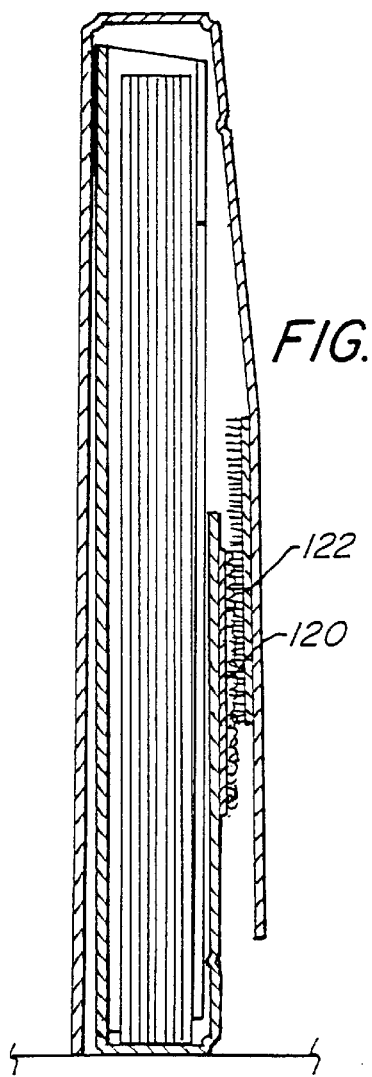
FIG. 25 is a sectional view along the line 25-25 of FIG. 21.
Figure 24:
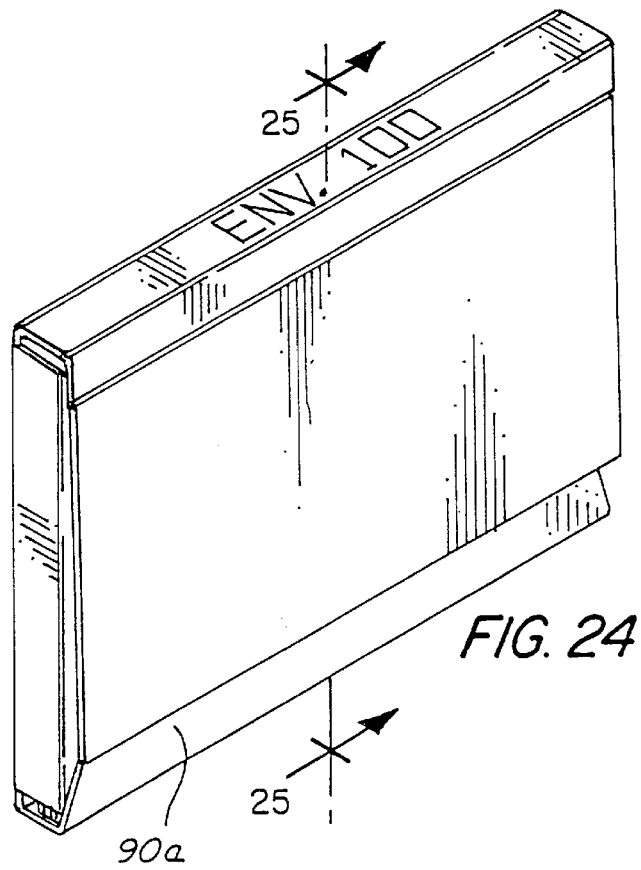
FIG. 24 is a perspective view of the closed embodiment of FIG. 23.

The embodiment of FIGS. 23–25 is similar to that of FIGS. 15–17 except that the flap 90a is provided with a hook and loop fastener 120 which cooperates with a hook and loop fastener 122 on the inside surface of the front panel.

Figure 26:
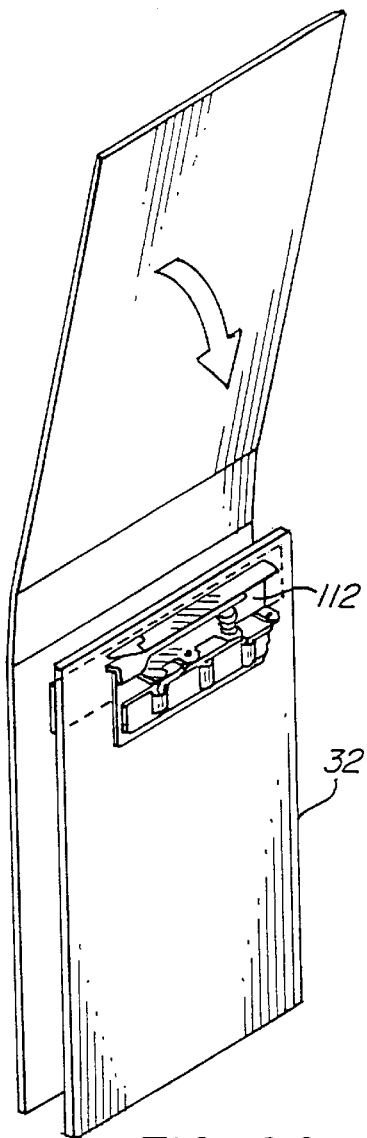
FIG. 26 is a perspective view of another embodiment of the folder of the present invention utilizing a clamp type fastener for securing the documents to the stiffener and an adhesive stripe for securing the stiffener to the back panel of the cover.

FIG. 26 shows a clamp fastener 112 mounted upon the stiffener 32.

Figure 27:
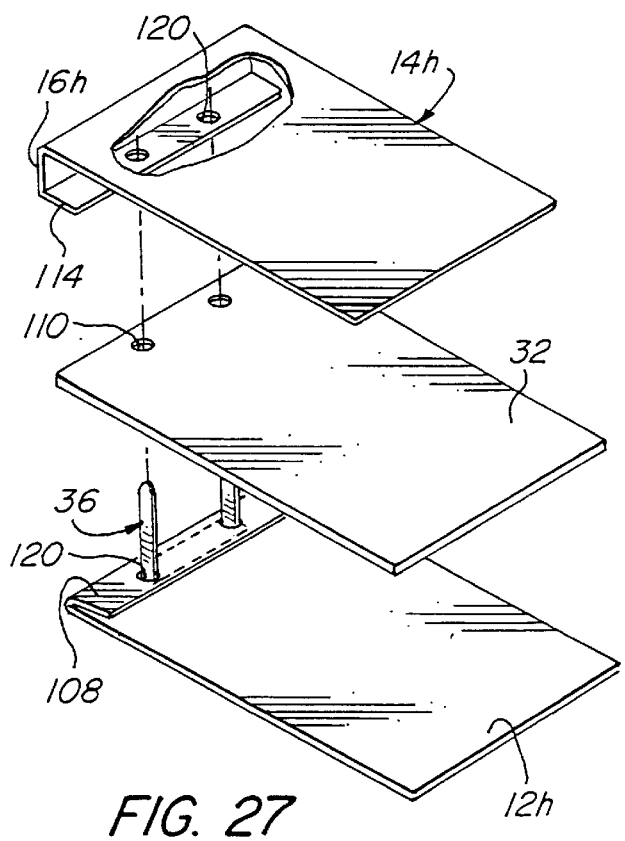
FIG. 27 is a perspective view of another embodiment of the present invention in which the cover is assembled from separate front and back panels which have overlying flaps through which a fastener extends to join the panels in assembly.

FIG. 27 shows another embodiment in which both panels 14h and 12h are separately formed and joined together by the fastener 36. The back panel 12h has an inturned flap 108 with apertures 120 through which the prongs of the fastener 36 extend. The prongs also extend through apertures 110 in the stiffener 32 and through an inturned flap 114 on the end of the spine 16h which is integrally formed with the front panel 14h. In the illustration, the clamp has been omitted for clarity.

Figure 28:
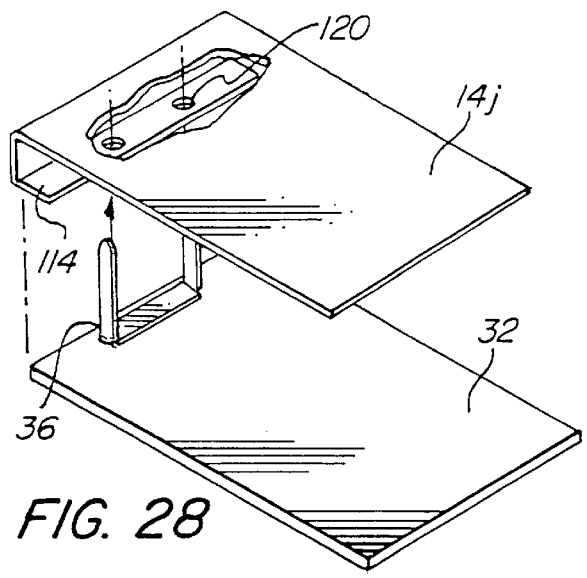
FIG. 28 is another embodiment in which the fastener is mounted upon the insert and extends through a flap on the front panel to secure it in assembly.

FIG. 28 is still another embodiment utilizing a separately formed front panel 14j with a flap 114 formed as in the prior embodiment and through which the prongs of the fastener 36 extend. However, in this instance the fastener 36 is secured to the surface of the stiffener 32.

Turning lastly to FIGS. 29 and 30, therein illustrated are folders produced in accordance with the present invention in which the spines 16 have been imprinted with indicia 20. These folders can be stored in an upright position on a shelf or table 118 as seen in FIG. 29 or in a box or drawer 120 as seen in FIG. 30.

The cover stock preferably a lightweight paperboard material such as the manila stock conventionally employed for manila folders. As has been previously indicated, the front and back panels can be formed integrally with the spine connecting them or they may be formed as separate elements with the spine formed as a component of one of them. If they are separate elements, one of the elements can be made of a printable paperboard or plastic stock and the other from a different material which may not be so readily imprinted and which may have a feature such as transparency for a particular application.

As will be appreciated, the covers and inserts may be separately stored and shipped, and assembled only after the cover has been printed. This enables substantial savings of time and money over a preassembled structure and also enables feeding the flexible cover through a printer.

Although the invention has been described in detail with reference to particular embodiments thereof, it will be apparent that upon a reading and understanding of the foregoing, numerous alterations to the described embodiments will occur to those skilled in the art and it is intended to include such alterations within the scope of the appended claims.

Thus, it can be seen from the foregoing detailed description and attached drawings that the document folder of the present invention provides a self-supporting structure which can be stacked in a vertical position, and which is easily removed from, and inserted into, a large number of such folders. The cover may be formed of relatively flexible and inexpensive paperboard stock, and is coupled with a relatively rigid member which can be fabricated from relatively rigid paperboard, plastic or other materials and assembled with the cover when the folder is placed into use. The spine connecting the covers is readily imprinted with indicia so as to allow facile identification of the contents of the folders when placed in a stack either horizontally or vertically.

Having thus described the invention, what is claimed is:

1. A document folder for enclosing and retaining a multiplicity of documents comprising:
   (a) a front cover element formed of relatively flexible sheet material and having a front panel and a spine hingedly connecting to said front panel, and a back panel element having a back panel, said panels being disposable in an overlying position and together with said spine providing an enclosure for receiving a multiplicity of documents therebetween, said spine being formed integrally with said front panel, said panels being movable relative to each other about said spine, the material of at least said spine and cover being imprintable;
   (b) a separately formed relatively rigid stiffener element dimensioned cooperatively with said back panel to rigidify said folder when stored vertically so that said folder is self-supporting when placed against and between vertical surfaces and will not collapse under its own weight; and
   (c) document securing means for securing a multiplicity of documents said stiffener element being secured in assembly with one of said back panel and stiffener element.

2. The document folder in accordance with claim 1 wherein said stiffener element is substantially coextensive with said back panel.

3. The document folder in accordance with claim 1 wherein said document securing means comprises a fastener having a center portion with a pair of prongs at its ends which extend through apertures in the stored documents.

4. The document folder in accordance with claim 1 wherein said front cover element and back panel element are integrally formed.

5. The document folder in accordance with claim 1 wherein said front cover element and back panel element are separate elements and said spine is integrally formed with said front panel.

6. The document folder in accordance with claim 1 wherein said document securing means is a clamp mounted on said stiffener element.

7. The document folder in accordance with claim 1 wherein said document securing means is a ring binder element mounted on said stiffener element.

8. The document folder in accordance with claim 1 wherein said document securing means comprises a pocket forming element on said stiffener element.

9. The document folder in accordance with claim 1 wherein said spine has a plurality of fold lines extending longitudinally thereof whereby said spine may be varied in width to vary the spacing between said panels.

10. An imprintable document folder for enclosing and retaining a multiplicity of documents comprising:
   (a) a single ply front cover element formed of relatively flexible sheet material and having a front panel and a spine hingedly connected thereto, the material of said front cover element being imprintable in an office printer;
   (b) a back cover element providing a back panel and secured to said spine, said front and back panels being disposable in an overlying position and together with said spine providing an enclosure for receiving a multiplicity of documents therebetween, said panels being movable relative to each other about said spine;
   (c) a relatively rigid stiffening means disposed on the inner surface of said back panel and dimensioned cooperatively with said back panel to rigidify said folder when stored vertically so that it is self-supporting when placed against and between vertical surfaces and will not collapse under its own weight; and
   (d) document securing means for securing a multiplicity of documents in said enclosure of said folder.

11. The imprintable document folder in accordance with claim 10 wherein there is included a coupling flap on said spine of said front cover element engageable with said back panel to secure said back panel to said spine.

12. The imprintable document folder in accordance with claim 10 wherein there is included at least one flap extending along at least one side of said back panel and foldable over said back panel to provide said stiffening means.

13. The imprintable document folder in accordance with claim 10 wherein said back panel element has flaps on three free sides of said back panel foldable over said back panel to provide said securing means.

* * * * *